United States Patent
Jandu et al.

(10) Patent No.: US 12,257,185 B2
(45) Date of Patent: Mar. 25, 2025

(54) CONVERTIBLE PHACOEMULSIFICATION I/A SLEEVE AND MECHANICAL ACTIVATION MECHANISM

(71) Applicant: JOHNSON & JOHNSON SURGICAL VISION, INC., Irvine, CA (US)

(72) Inventors: Harkirat S. Jandu, Tustin, CA (US); Mark W. Ross, Costa Mesa, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 782 days.

(21) Appl. No.: 17/305,508

(22) Filed: Jul. 8, 2021

(65) Prior Publication Data
US 2021/0330497 A1    Oct. 28, 2021

Related U.S. Application Data

(62) Division of application No. 16/005,519, filed on Jun. 11, 2018, now Pat. No. 11,058,578.

(60) Provisional application No. 62/519,786, filed on Jun. 14, 2017.

(51) Int. Cl.
*A61F 9/00* (2006.01)
*A61F 9/007* (2006.01)
*A61M 1/00* (2006.01)
*A61B 17/32* (2006.01)

(52) U.S. Cl.
CPC ...... *A61F 9/00745* (2013.01); *A61F 9/00736* (2013.01); *A61M 1/85* (2021.05); *A61B 2017/320084* (2013.01); *A61B 2218/002* (2013.01); *A61B 2218/007* (2013.01); *A61M 1/774* (2021.05)

(58) Field of Classification Search
CPC ... A61F 9/00745; A61F 9/00736; A61M 1/85; A61M 1/774; A61B 2017/320084; A61B 2218/002; A61B 2218/007
See application file for complete search history.

(56) References Cited

U.S. PATENT DOCUMENTS

| | | | |
|---|---|---|---|
| 5,188,589 | A | 2/1993 | Wypych et al. |
| 5,217,465 | A | 6/1993 | Steppe |
| 5,282,786 | A | 2/1994 | Ureche |
| 5,354,265 | A | 10/1994 | Mackool |
| 5,437,678 | A | 8/1995 | Sorensen |

(Continued)

FOREIGN PATENT DOCUMENTS

| CN | 106175848 A | 12/2016 |
|---|---|---|

OTHER PUBLICATIONS

International Search Report and Written Opinion for Application No. PCT/IB2018/054243, mailed on Sep. 26, 2018, 14 pages.

*Primary Examiner* — Jason E Flick

(57) ABSTRACT

A system and method for provided a phacoemulsification surgery handpiece including a convertible sleeve for phacoemulsification surgery and irrigation/aspiration procedures. In a retracted state, the sleeve is in a desired relationship with the exposed portion of a phaco tip of the handpiece to support normal phacoemulsification surgery. In an extended state, the sleeve features a distally placed aspiration hole located forward from the distal end of a phaco tip to allow typical irrigation/aspiration procedures. A distal tip segment of the hand piece is overmoldedby polyimide materials having a split feature to allow egress of a phaco tip.

14 Claims, 14 Drawing Sheets

(56) References Cited

U.S. PATENT DOCUMENTS

| | | | | |
|---|---|---|---|---|
| 5,667,489 | A | * | 9/1997 | Kraff .................. A61F 9/00745 604/35 |
| 5,830,192 | A | | 11/1998 | Van Voorhis |
| 5,941,887 | A | * | 8/1999 | Steen .................. A61F 9/00745 606/107 |
| 6,013,046 | A | | 1/2000 | Maaskamp et al. |
| 7,857,794 | B2 | | 12/2010 | Dimalanta et al. |
| 2002/0052609 | A1 | * | 5/2002 | Chen .................. A61F 9/00736 606/107 |
| 2004/0153026 | A1 | | 8/2004 | Mackool |
| 2012/0116290 | A1 | | 5/2012 | Dimalanta et al. |
| 2012/0143125 | A1 | * | 6/2012 | Lane .................. A61M 1/85 604/35 |
| 2012/0157934 | A1 | * | 6/2012 | Liao .................. A61F 9/00745 604/264 |
| 2013/0289469 | A1 | | 10/2013 | Hong |
| 2014/0052053 | A1 | | 2/2014 | Hong et al. |
| 2014/0276377 | A1 | | 9/2014 | Chang et al. |

* cited by examiner

CONVERTIBLE PHACOEMULSIFICATION I/A SLEEVE AND MECHANICAL ACTIVATION MECHANISM

PRIORITY

The present application is a divisional application of and claims priority to U.S. patent application Ser. No. 16/005,519, filed Jun. 11, 2018, which claims priority to U.S. Provisional No. 62/519,786, filed Jun. 14, 2017, which are hereby incorporated by reference.

FIELD OF THE INVENTION

The present invention relates generally to providing a phacoemulsification surgical device and, more particularly, is directed to providing a convertible phacoemulsification irrigation and aspiration sleeve for phacoemulsification surgery.

DESCRIPTION OF THE BACKGROUND

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

As may be appreciated, the flow of fluid to and from a patient through a fluid infusion or extraction system, and thus the control of fluids and fluid pressure through the phacoemulsification handpiece, is critical to the procedure performed. Different medically recognized techniques have been utilized to control the fluid flow during the lens removal portion of the surgery. Among these, one popular technique is a simultaneous combination of phacoemulsification, irrigation and aspiration using a single handpiece. This method includes making the incision, inserting the handheld surgical implement to emulsify the cataract or eye lens, and, simultaneously with this emulsification, having the handpiece provide a fluid for irrigation of the emulsified lens and a vacuum for aspiration of the emulsified lens and inserted fluids.

Currently available phacoemulsification systems, such as those mentioned above, typically include a variable speed peristaltic pump and/or vacuum pump, a vacuum sensor, an adjustable source of ultrasonic power, and a programmable microprocessor with operator-selected presets for controlling aspiration rate, vacuum and ultrasonic power levels. The phacoemulsification handpiece is interconnected with a control console by an electric cable for powering and controlling a piezoelectric transducer that drives the action of the handpiece. Tubing provides irrigation fluid to the eye through the handpiece and enables withdrawal of aspiration fluid from an eye through the handpiece.

Generally, irrigation and aspiration are employed by the surgeon using the device to remove unwanted tissue and maintain pressure within the eye. Moreover, the use of, and particularly the pressurization of, the irrigation fluid is critical and may, for example, prevent the collapse of the eye during the removal of the emulsified lens. Irrigation fluid pressure is also used to protect the eye from the heat generated by the ultrasonic cutting needle and may suspend fragments created during the surgery in fluid for more easy removal through aspiration.

Irrigation fluid pressure has been conventionally handled in two ways. The first method to increase irrigation fluid pressure has relied upon the height of the fluid source. Conventional IV poles may be adjusted in height to create the desired pressure head using gravity-feed principles. The second method includes the use of an infusion pump either directly pumping the fluid typically in the form of a peristaltic pump used in-line with an irrigation delivery line or by pressurizing the fluid container thus increasing higher atmosphere above the fluid resulting in higher infusion pressure and flow to the surgical site.

In the aforementioned configurations, combining phacoemulsification, irrigation and aspiration, the handpiece may be configured to provide a fluid for irrigation of an emulsified lens and a vacuum for aspiration of the emulsified lens and inserted fluids. In such configurations fluidics lines are typically switched from phacoemulsification to irrigation and aspiration. While the configuration provides advantages for the surgical procedure, the switching of fluidics lines unnecessarily slows down the procedure and creates the potential for fluid to drain accidentally. Furthermore, the switching of lines has the tendency to introduce fluctuations of intra-ocular pressure.

Thus, there is a need for a system and method that provides a surgical process that does not require a separate phacoemulsification and I/A hand piece, and therefore reduce insertions and withdrawals.

SUMMARY OF THE INVENTION

A surgical hand piece is provided wherein a convertible sleeve encapsulates at least part of the surgical hand piece. A system and method may be utilized to place the sleeve in alternative states. The system and method may include at least one initial state to place the sleeve in position for normal phacoemulsification surgery and a subsequent state to place the sleeve in position for typical irrigation/aspiration mode. The hand piece allows for lateral movement of the sleeve and may be manually controlled and/or at least partially automated.

A surgical hand piece in accordance with another embodiment of the present invention is provided, the surgical hand piece may be fitted with a bullet-nose cover as part of the convertible sleeve. The bullet-nose cover may be comprised of polyimide materials and allows for alternative modes of phacoemulsification and irrigation/aspiration.

BRIEF DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION OF THE INVENTION

Figure 1:
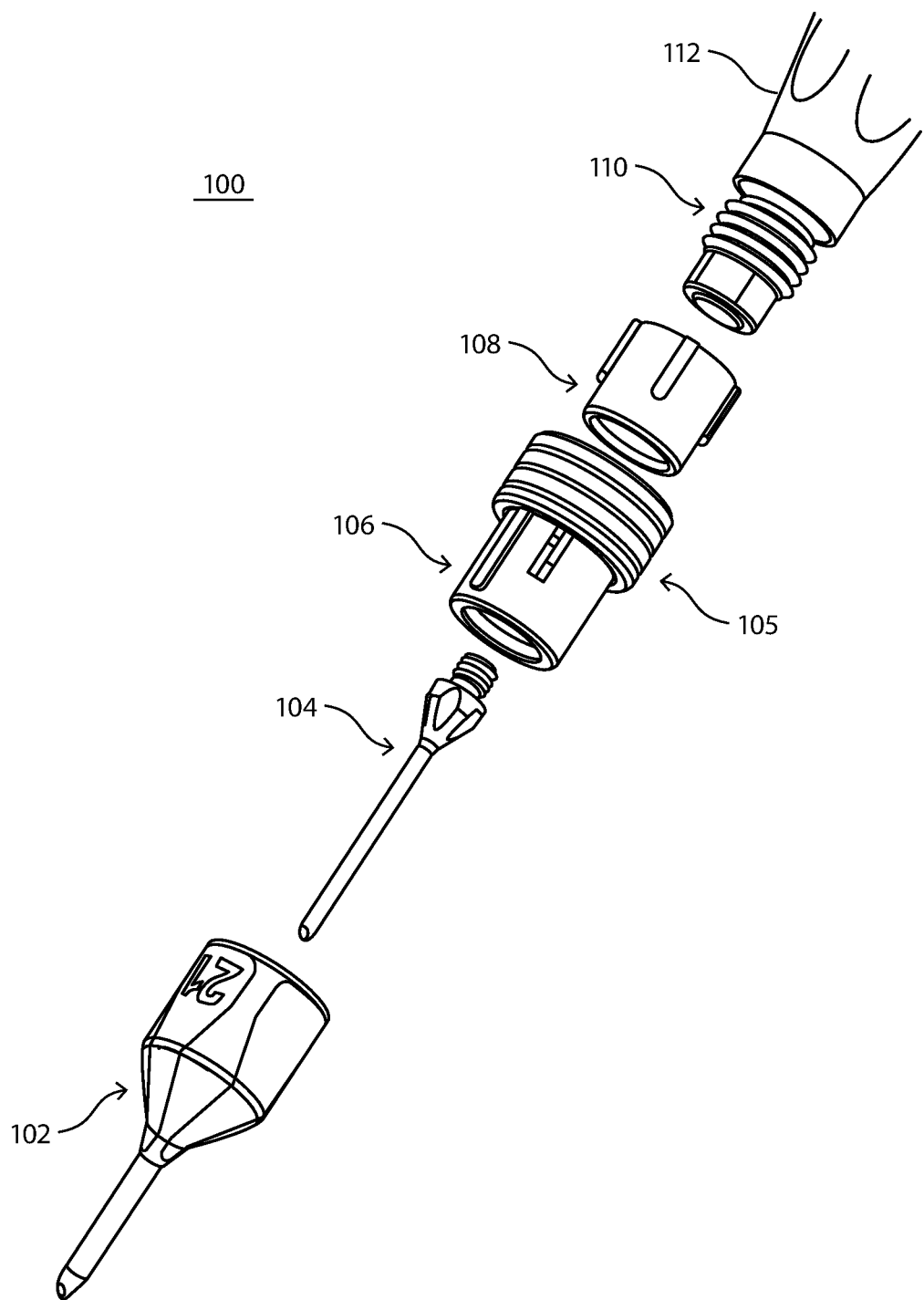
FIG. 1 illustrates a exploded view of a surgical handpiece of the present invention.

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

In an embodiment of the present invention a convertible sleeve of a surgical handpiece may be in a retracted, or initial, state, which may place the sleeve in a desired relationship with the exposed distal portion of the phacoemulsification tip to support normal phacoemulsification in the same manner as current practice. In another embodiment of the present invention, a convertible sleeve of a surgical handpiece may be in an extended state. The sleeve may include a distally placed aspiration hole located forward from the distal end of a phacoemulsification tip allowing for typical irrigation/aspiration ("IA") activities to occur. The aspiration hole may be placed roughly perpendicular to the bevel surface at the end of the sleeve, for example. Surfaces adjacent to the aspiration hole may be used for capsule polishing and may be altered to best perform the intended purpose. Irrigation outflow holes on the sleeve may be located slightly further back proximally adjacent to a seal feature of the sleeve for the tip. The irrigation outflow holes may be angulated, for example, and both the irrigation and aspiration holes may be kerf, chamfered, beveled, rounded, or otherwise not substantially square to the face to the device.

In a further embodiment of the present invention, an adaptor may be installed, for example, screwed, onto existingthreads on the distal end of a standard phacoemulsification hand piece, such as a standard AMO® hand piece, followed by a hub component, subsequently allowing mounting of a sleeve. The hub component may comprise a sliding hub which may further comprise an actuator enabling the movement of the sleeve along the length of the phacoemulsification tip. The sliding hub may also control the amount of linear movement allowed. For example, the sliding hub may be keyed and may be regulated in that it may self-register (align) and latch, allowing for re-positioning after, for example, the I/A portion of the procedure, should additional phacoemulsification be needed.

The lateral movement of the sleeve may be manually controlled and/or at least partially automated. For example, the user of the hand piece may be able to easily move the sleeve forwards and backwards along an axis of the adapter in concert with one or more grooves or reliefs correspondent to the sliding hub. The friction between the hub and adapter, for example, may prove sufficient to resist unwanted movement of the sleeve. A locking mechanism may also be used to retain the sleeve and hub in a desired position and may comprise a latch, a detent and corresponding relief, and other engagements which may prevent unwanted movement. Movement of the sleeve and hub may also be at least partially mechanical and may allow a user to use a remote device, such as a foot pedal, to control the movement of the sleeve. By way of example, the hub may be communicatively connected to a motor and/or electromagnetic assembly which may provide for hands-free lateral movement of the sleeve.

In yet another embodiment of the present invention, a more remote or proximally-oriented location on a surgical hand piece for an actuator to position the sleeve may be preferred. Alternate materials for consideration for the convertible sleeve may be higher shore diameter silicone (90A+) or TPE medias (for additional axial stiffness). In an embodiment of the present invention, at least a portion of the sleeve may be composed oftwo or more layers and may, for example, be composed of a two-layer system wherein the second layer provides rigidity to the first layer. For example, a soft silicone may be used fora top layer and a more rigid plastic used as the second layer to provide a desired amount of support and rigidity of the top layer.

Ribbed features inside the annular portion of the convertible sleeve cannula may also be used. For example, ABS, and other related plastics, may be considered for the convertible sleeve construction using a TPE or silicone over molded shaft and tip end, thereby providing other opportunities to provide connective means of actuation of the mechanism and retain the soft requirements desired of the distal tip end portion. Other means of achieving axial stiffness may also include an extruded PTFE tube used as a support liner inserted into the interior diameter of the sleeve shank after molding.

It is to be understood that the convertible sleeve may be molded into alternative shapes, such as a curved shape, or with specific distal angulations which may be achieved by molding into a desired shape. Even further, a sleeve may be straight-molded to conform to a curved or angulated phacoemulsification tip.

As illustrated in FIG. 1, diagram 100 shows an exploded view of a surgical instrument in accordance with a typical embodiment of the present invention. Diagram 100 illustrates sleeve 102 encapsulating, at least partially, needle 104 and hub adaptor 106, which may be removeably attached to the hand piece 112. As mentioned above, certain adaptors may be employed to aid in operation of the sleeve 102. For example, the instrument may include a hub adaptor 106 and a hand piece adaptor 108. Hand piece adaptor 108 may be secured to the instrument utilizing handpiece threads 110 and hub adaptor 106 may be slidably resident on adaptor 108. Sleeve 102 may slidably fit onto hub adaptor 106 and may removably engage with attachment portion 105 mechanically and/or through a friction fit, for example. Mechanical means may take the form of threads and/or other mated and non-mated protrusions and recesses, either on adaptor 106 and/or within the body of sleeve 102.

Figure 2A:
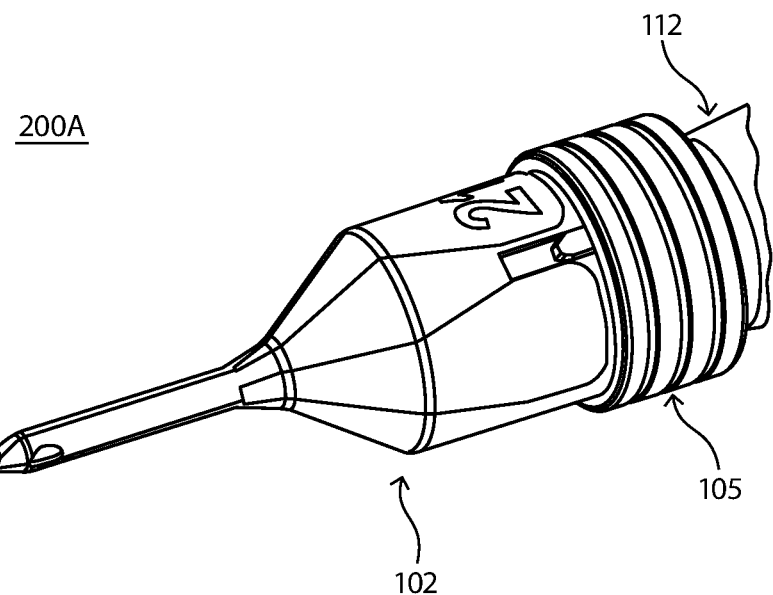
FIGS. 2A and 2B illustrate an extended and retracted position of a convertible sleeve of a surgical hand piece of the present invention.
Figure 2B:
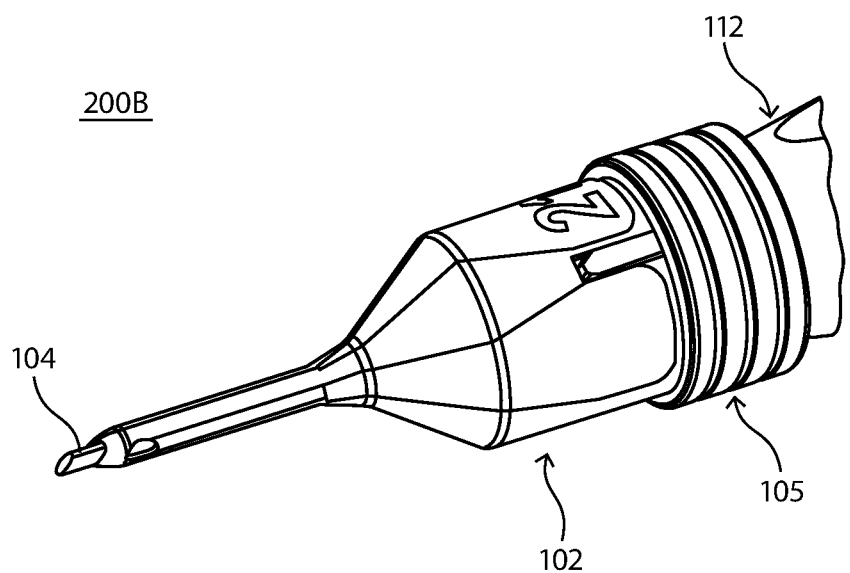
Figure 3A:
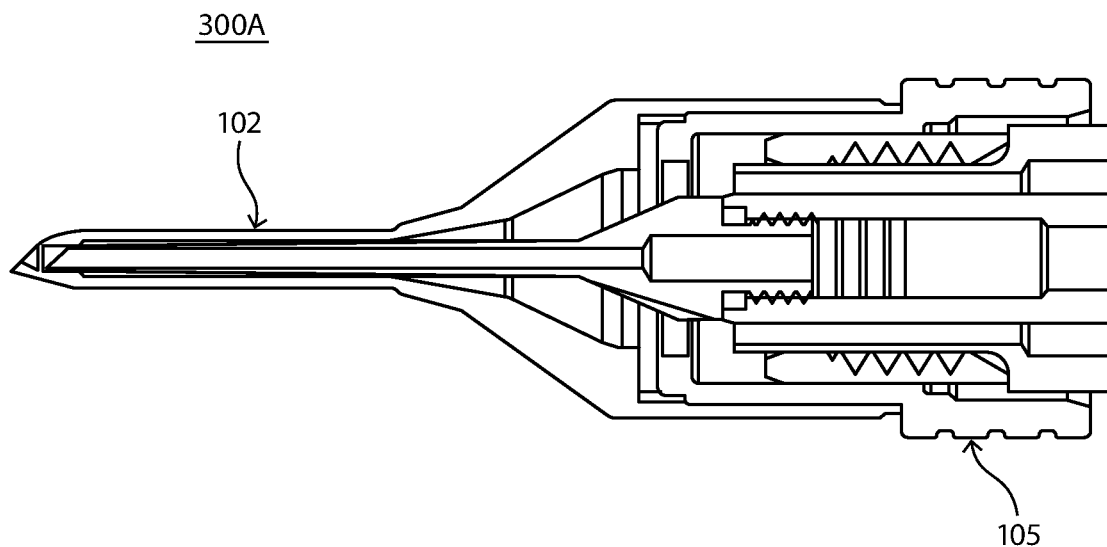
FIGS. 3A and 3B illustrate a cross-section view of an extended and retracted position of a convertible sleeve of a surgical hand piece of the present invention.
Figure 3B:
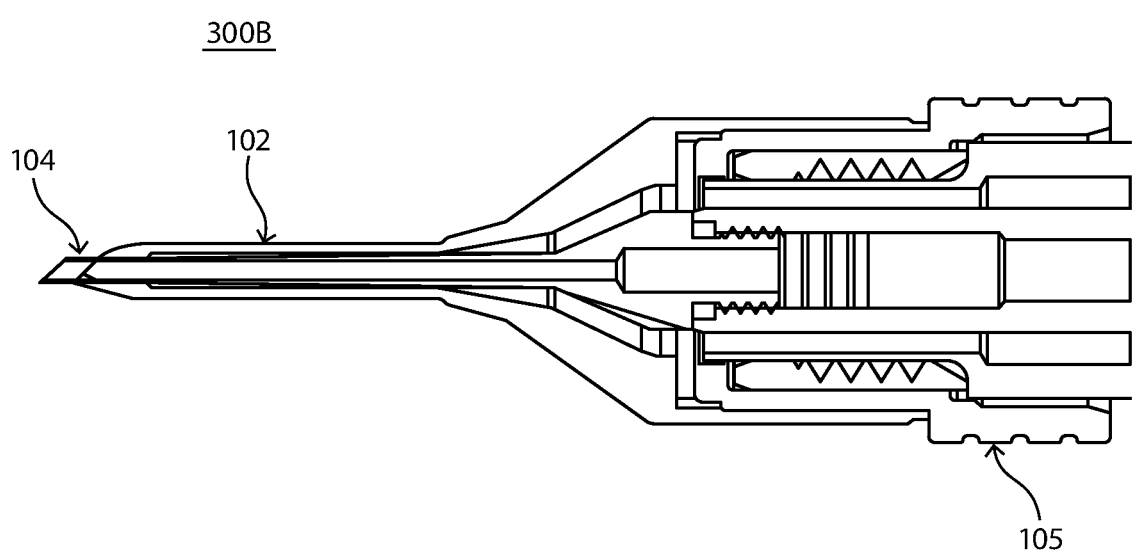

As illustrated in FIGS. 2A and 2B, diagram 200A and 200B show the surgical instrument in an extended position and a retracted position, respectively. For example, in 200A, sleeve 102 is in an extended position and needle 104 (not shown) is in a retracted position, allowing for typical I/A activities to occur. Also shown is attachment portion 105 and handpiece 112. In 200B, sleeve 102 is in a retracted position allowing for typical phacoemulsification surgical procedures. As shown, needle 104 is in the extended position. Also shown is attachment portion 105 and handpiece 112. As illustrated in a cross-sectional view of FIGS. 3A and 3B, diagram 300A shows sleeve 102 in an extended position and 300B shows sleeve 102 in a retracted position.

Figure 4:
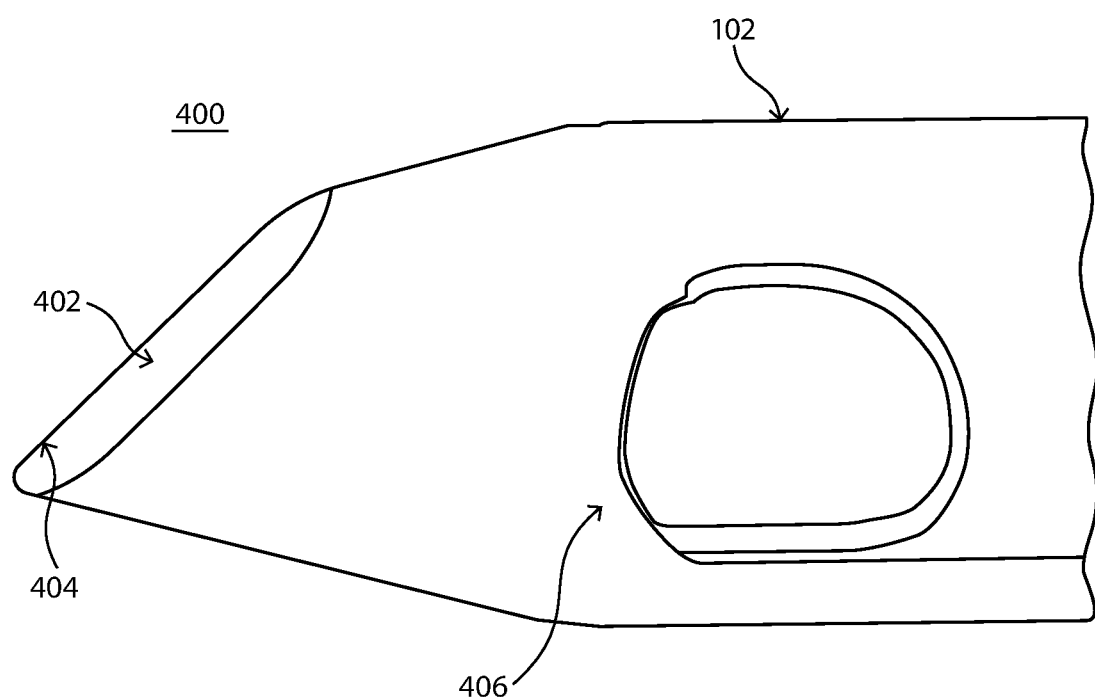
FIG. 4 illustrates a side elevation close up of a surgical hand piece of the present invention.

As illustrated in FIG. 4, diagram 400 shows a side elevation close-up of the surgical instrument with sleeve 102 in an extended position and needle 104 (not shown) in a retracted position. Aspiration port 402 is shown being at an angle of 45° and having a diameter of 0.5 mm, for exemplary purposes. Extended portion 404 of sleeve 102 may be used for polishing and/or removal of lens epithelial cells from the interior part of the capsular bag. Sleeve 102 may also include angle flow ports 406. It is understood that ports, such as the aspiration port and irrigation ports, may be at different angles with varying diameters.

Figure 5:
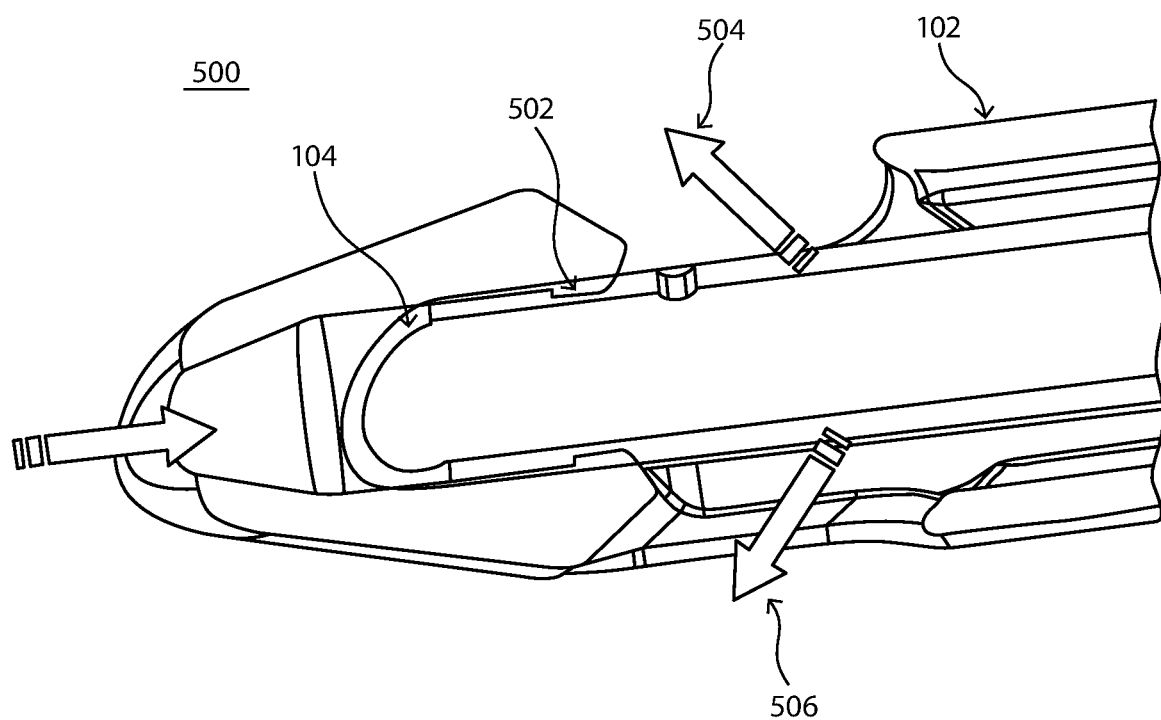
FIG. 5 illustrates a top cross-section close up of flow ports and tip seal of a surgical hand piece of the present invention.

As illustrated in FIG. 5, diagram 500 shows a top cross-section close-up of flow ports 504 and 506 of sleeve 102. As shown by the arrows in FIG. 5, fluid flow exits irrigation ports 504 and 506. In one preferred embodiment, fluid may flow along a channel surrounding the needle 104. Sleeve 102 may also include a sleeve tip seal 502. The tip seal 502 may be a radial lip seal inside the sleeve 102 intended to choke off/prevent any fluid from discharging anywhere other than through the irrigation ports. Body of the sleeve 102 may engage with needle 104 to provide a seal after ports 504 and 506. This seal may prevent back flow and restricts fluid discharge to ports 504 and 506.

Figure 6:
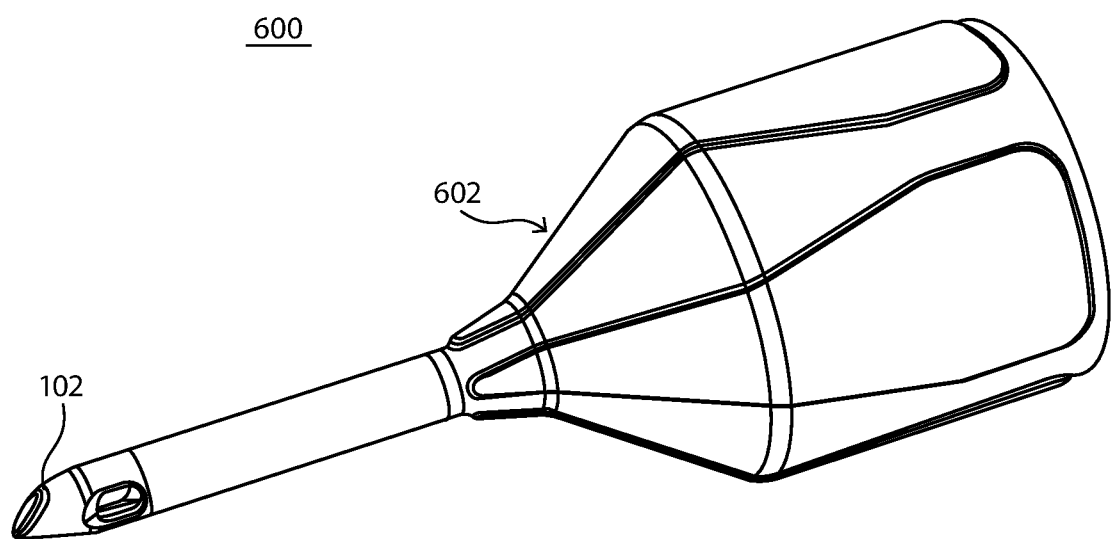
FIG. 6 illustrates an implementation of silicone or TPE sleeve with an overmolded external stiffening jacket of a surgical hand piece of the present invention.
Figure 7:
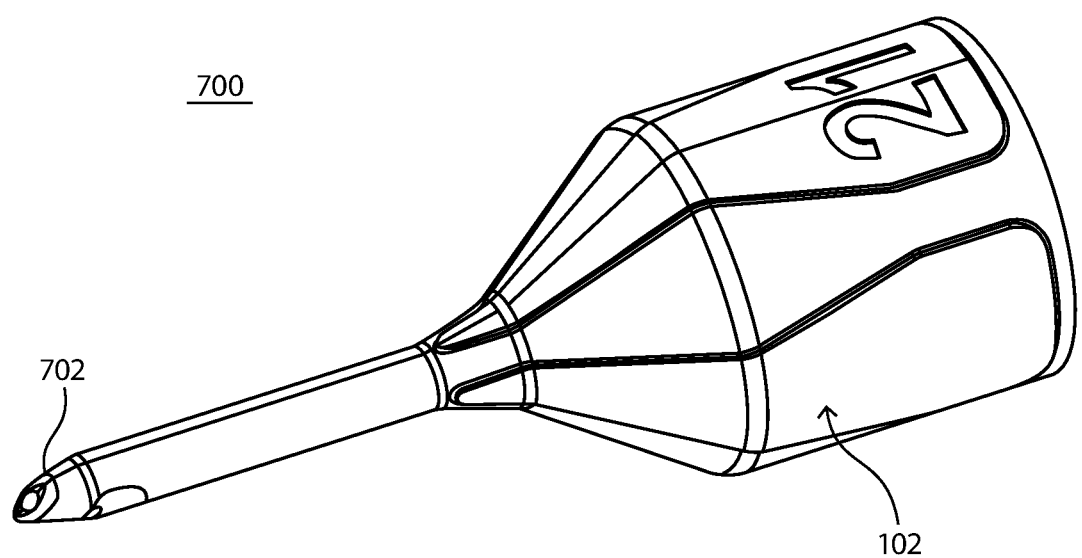
FIG. 7 illustrates an implementation of silicone or TPE sleeve with a PTFE inserted liner of a surgical handpiece of the present invention.
Figure 8:
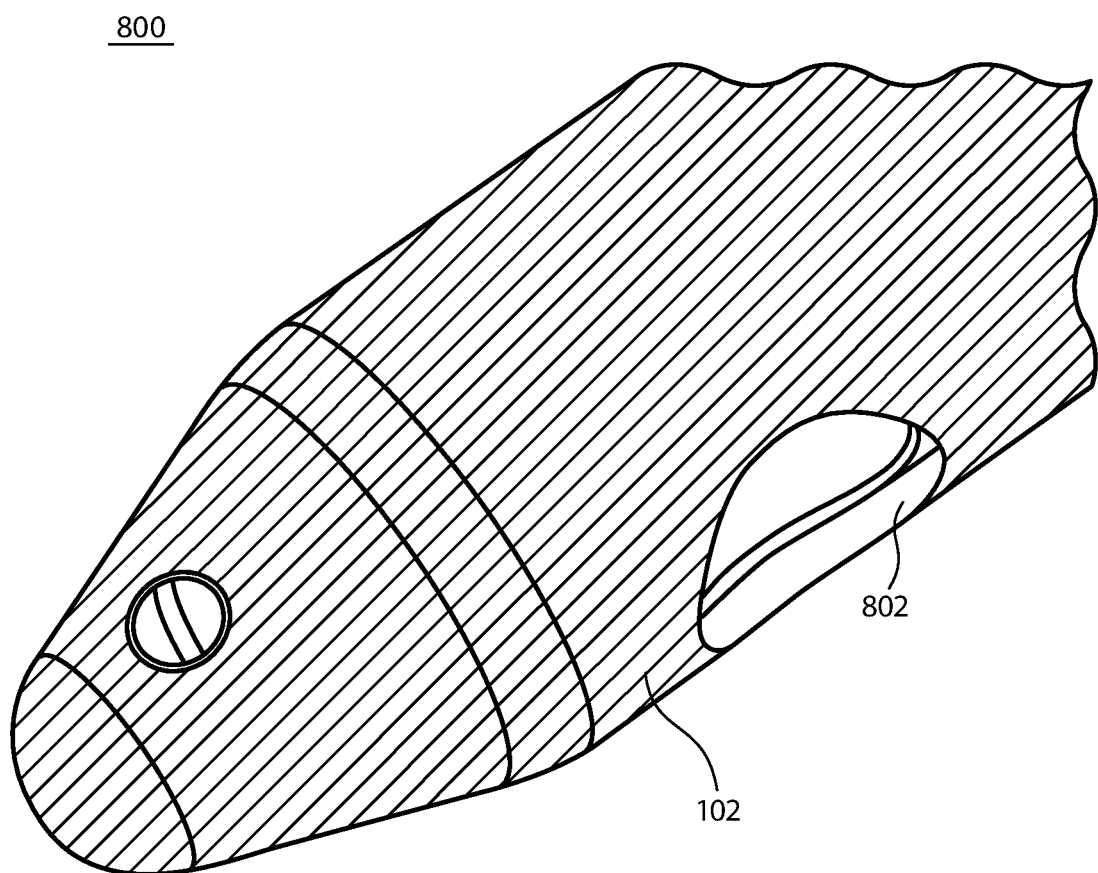
FIG. 8 illustrates an implementation of an ABS sleeve with silicone or TPE overmolded shank and distal tip segment of a surgical handpiece of the present invention.
Figure 9:
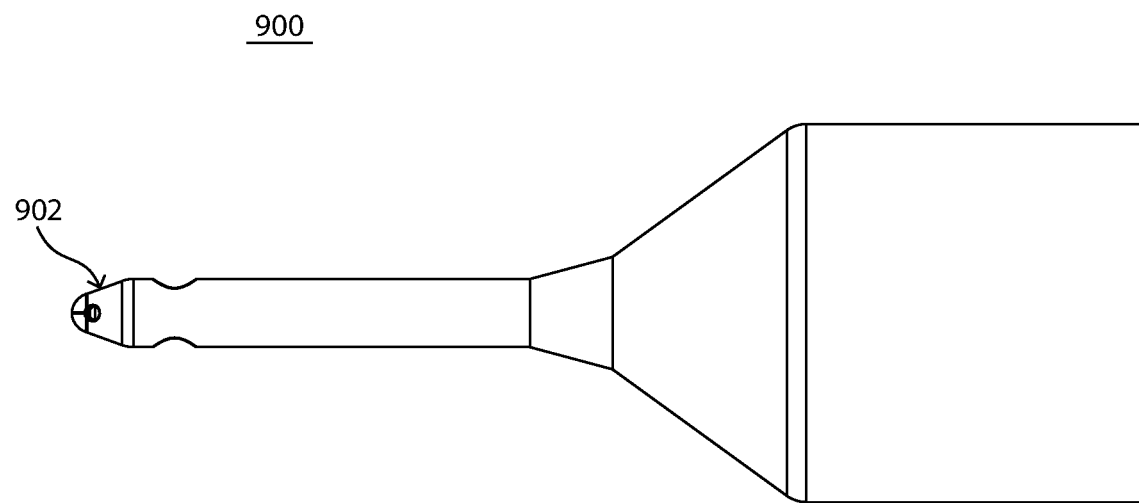
FIG. 9 illustrates a side elevation close up of a surgical hand piece of the present invention.

FIGS. 6-8 illustrate the implementation of alternative materials that may be used for sleeve 102. Diagram 600 of FIG. 6 shows an exemplary implementation of a Silicone or TPE sleeve 102 with an overmolded external stiffening jacket 602. The external stiffening jacket 102 may prevent the lumen of the sleeve from buckling or sticking to the shaft of the surgical tip when translating between I/A or phacoemulsification modes. For example, when the needle switches between an extended or retracted position.

Diagram 700 of FIG. 7 shows another exemplary implementation of a silicone or TPE sleeve 102 with a PTFE inserted liner 702. Diagram 800 of FIG. 8 shows an exemplary implementation an ABS sleeve 102 (shaded) with a silicone or TPE overmolded shank and a distal tip segment 802. It is to be understood that different materials may be utilized alone or in combination within the scope of the present invention.

Figure 10:
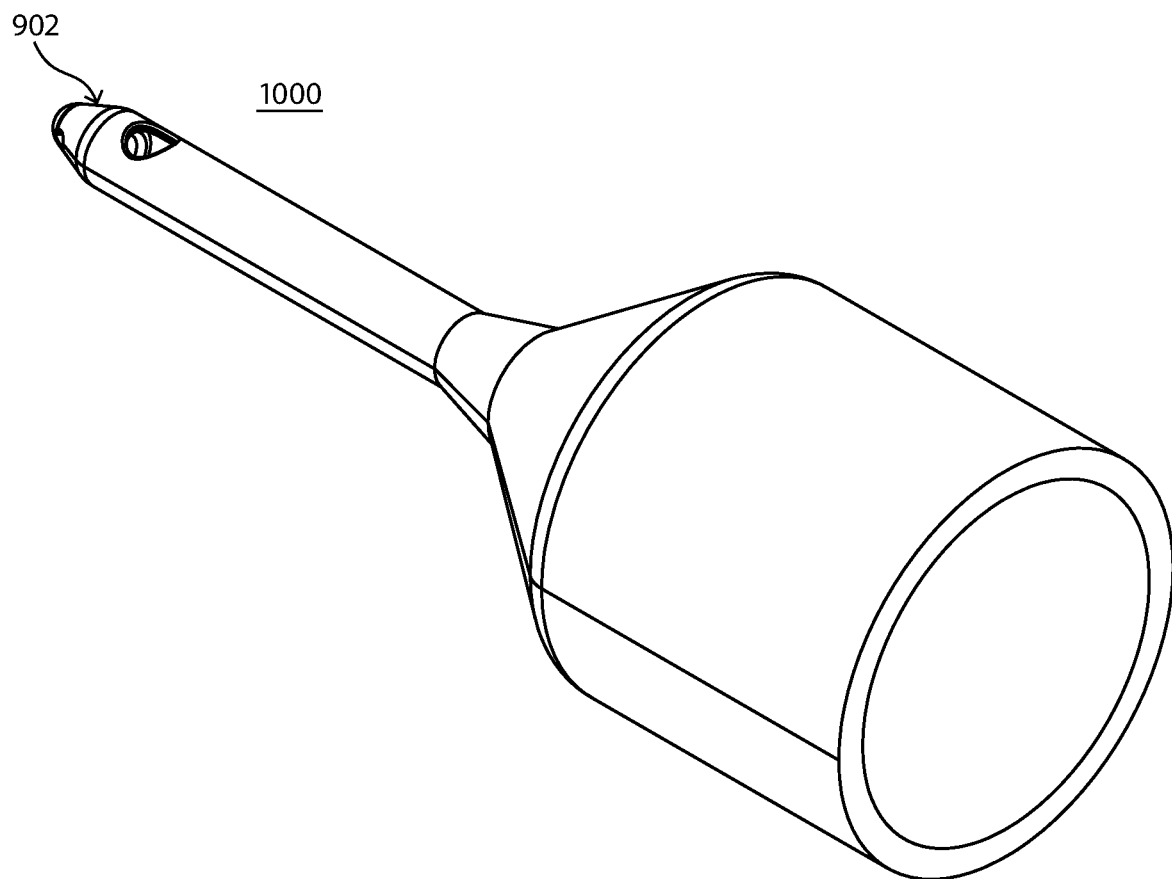
FIG. 10 illustrates a cross-sectional view of a surgical hand piece of the present invention.
Figure 11:
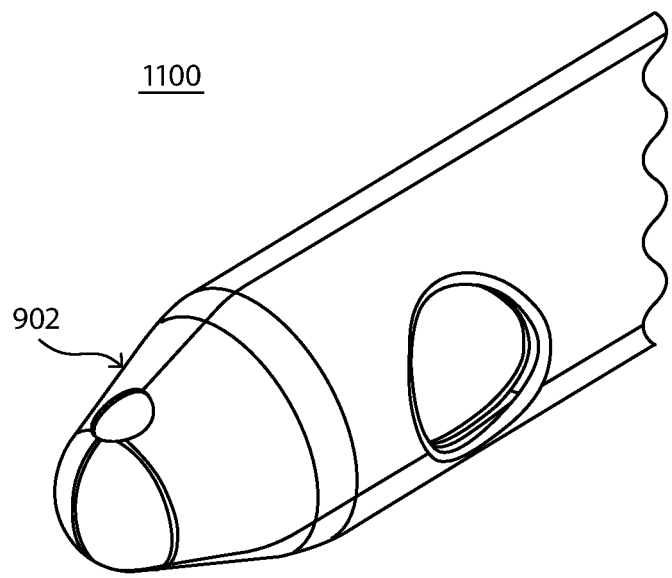
FIG. 11 illustrates a side elevation close-up of a surgical hand piece of the present invention.
Figure 12:
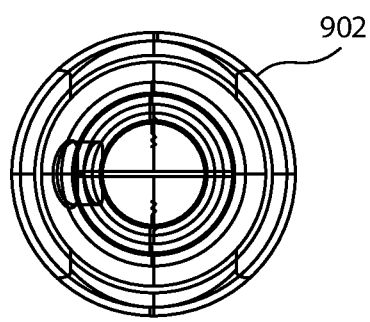
FIG. 12 illustrates an implementation of a bullet-nose implementation of a surgical handpiece of the present invention.
Figure 13:
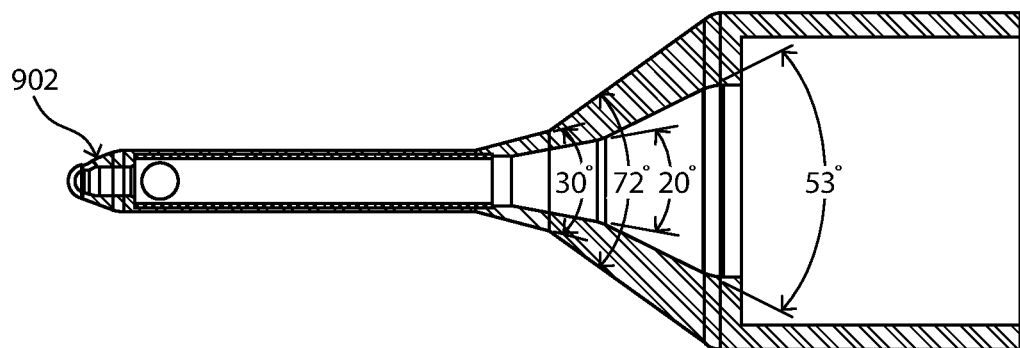
FIG. 13 illustrates a front view of a bullet-nose implementation of a surgical handpiece of the present invention.

As illustrated in FIGS. 9-12, the surgical hand piece distal tip segment may comprise a bullet-nose shaped tip 902, in which in an embodiment it may be overmolded to a portion of the surgical handpiece and may be comprised of polyimide materials. The implementation of a polyimide liner may reinforce the lumen of the sleeve described herein above. FIG. 13 illustrates a side-view cross-section of the surgical hand piece described above and as shown in FIGS. 9 and 12. FIG. 13 illustrates different angled segments which are all deemed exemplary. Different angled segments allows for smooth operation of the surgical handpiece and proper fluid flow during aspiration/irrigation, or the like. FIGS. 10 and 11 illustrate simplified side cross-sectional views of the surgical hand piece as shown and described above with respect to FIGS. 3A and 3B.

Figure 14:
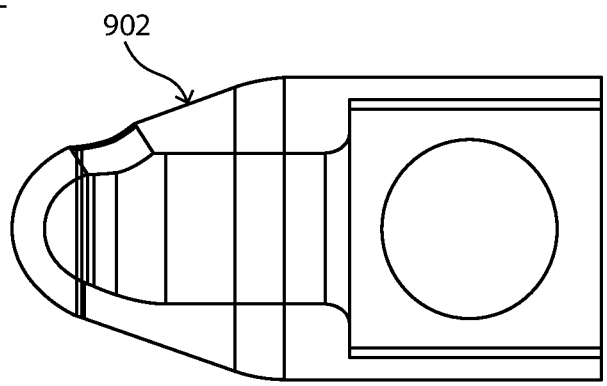
FIG. 14 illustrates a cross-sectional view of a surgical hand piece of the present invention.

FIG. 14 illustrates another exemplary embodiment of the disclosed invention. As shown in FIG. 14, another side-view of the surgical instrument having a distal tip segment may be overmolded by a bullet-nose shaped tip 902 comprised of polyimide materials.

Figure 15:
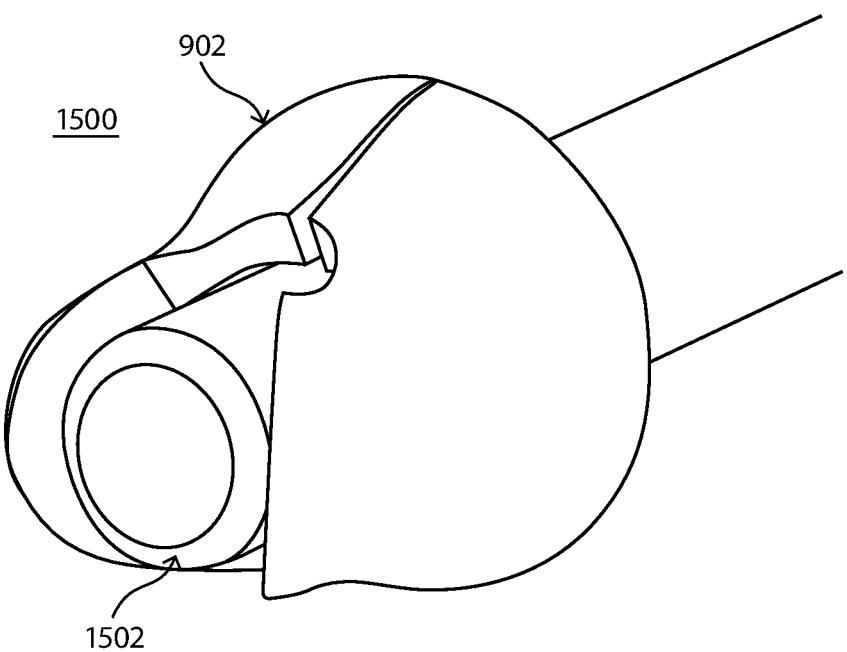
FIG. 15 illustrates a close-up view of the surgical hand piece of FIG. 14.
Figure 16:
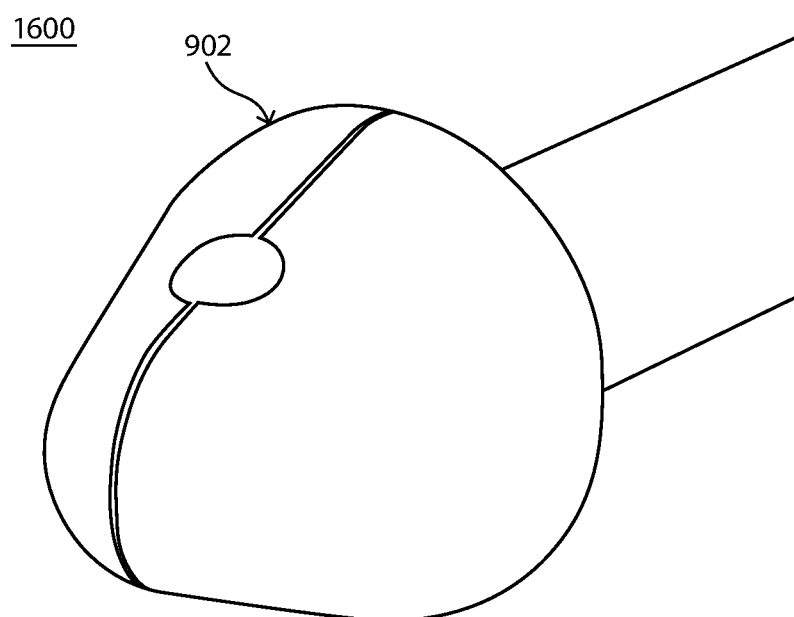
FIG. 16 illustrates the surgical hand piece in an extended state in accordance with an embodiment of the disclosed invention.
Figure 17:
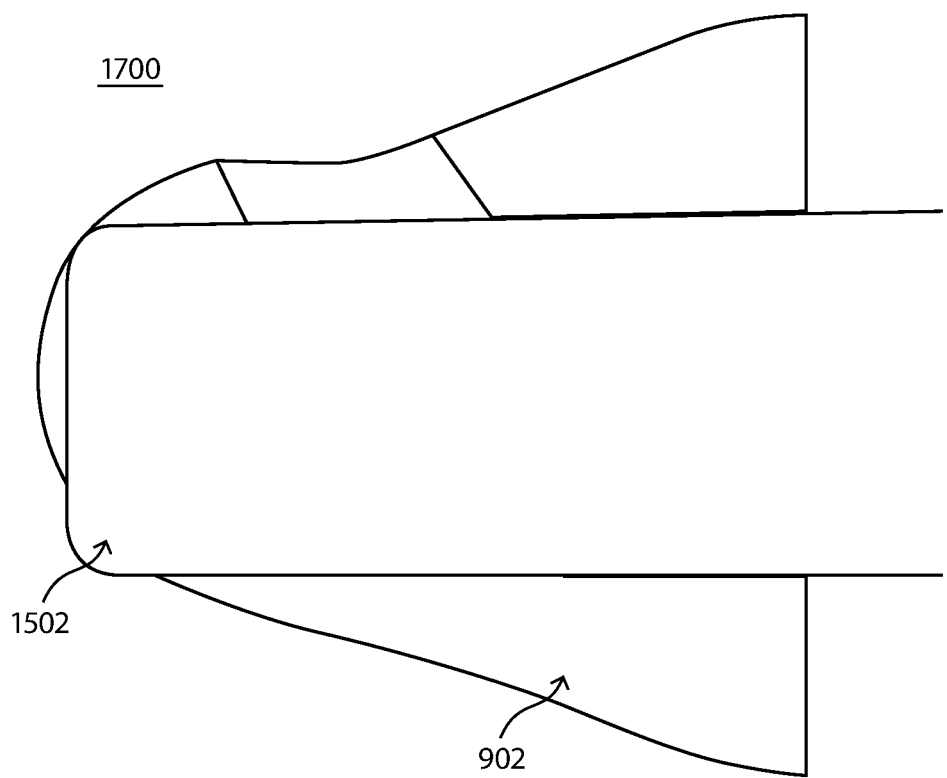
FIG. 17 illustrates the surgical hand piece in a retracted state in accordance with an embodiment of the disclosed invention.
Figure 18:
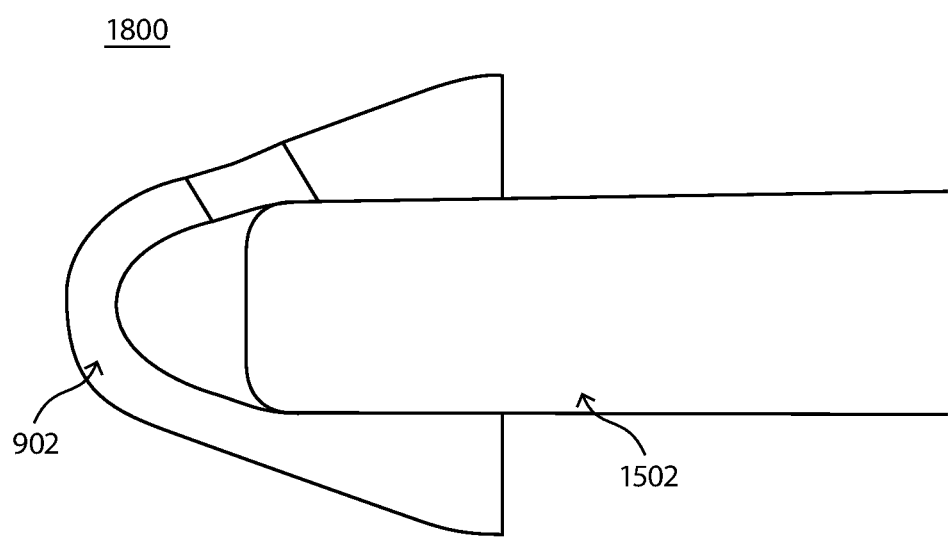
FIG. 18 illustrates the surgical hand piece from a side view in accordance with an embodiment of the disclosed invention.
Figure 19:
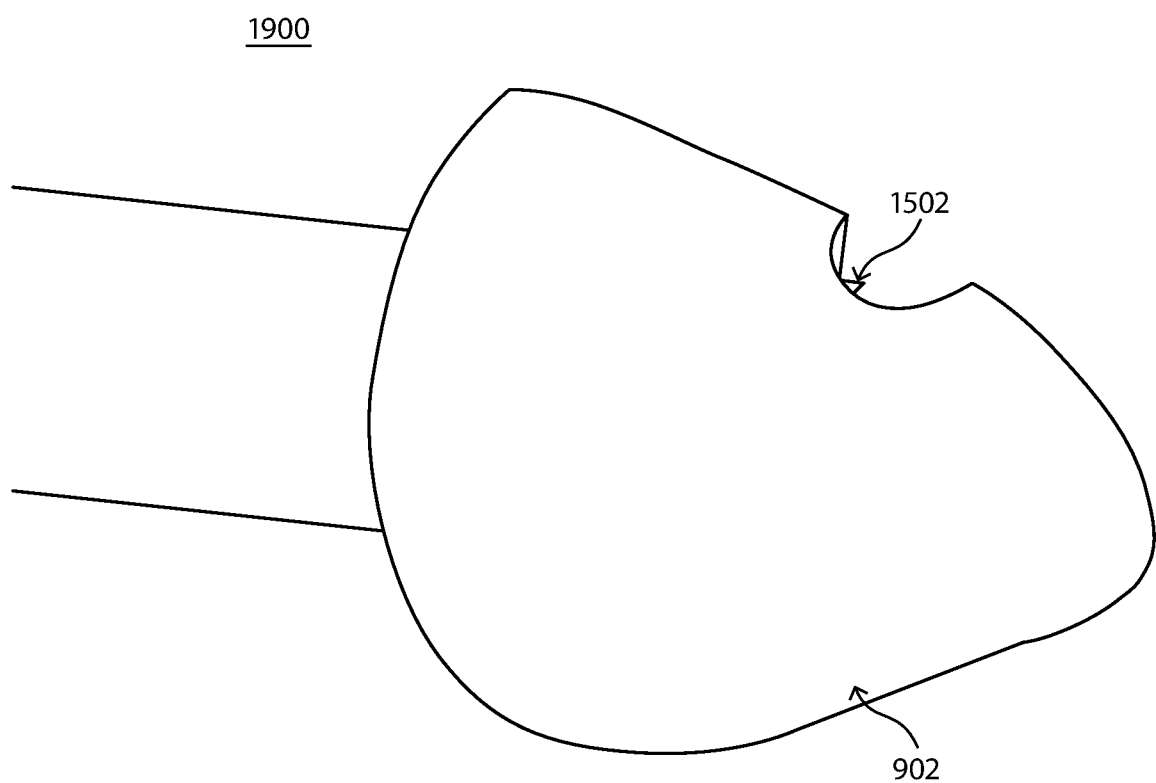
FIG. 19 illustrates the surgical hand piece from a side view in accordance with an embodiment of the disclosed invention.

As illustrated in FIGS. 15-17, the distal tip segment overmolded by a bullet-nose tip 902 may include a split or slit feature at the distal end to facilitate egress of a surgical needle 1502, such as a phaco needle. As shown in diagram 1500 of FIG. 15, when extended, the needle 1502 may push through a split/slit feature of the bullet-nose tip sleeve 902 (see FIG. 16) to allow for phacoemulsification, or the like. As shown in diagram 1600 of FIG. 16, when needle 1502 is retracted, the split/slit feature 902 of the tip may self-collapse to create a seal, thereby converting the surgical instrument and allowing for aspiration and/or irrigation only (see FIGS. 17 and 19, diagrams 1700 and 1900). FIG. 18 shows, in diagram 1800, the phaco tip 1502 in a retracted state.

Those of ordinary skill in the art may recognize that many modifications and variations of the herein disclosed systems and methods may be implemented without departing from the spirit or scope of the invention. Thus, it is intended that the present invention covers such modifications and variations provided they come within the scope the appended claims and their equivalents.

What is claimed is:

1. A surgical handpiece, comprising:
 a hub attached to the handpiece;
 a sleeve positioned over an outer portion of the hub, wherein the sleeve is configured to be slidably moved in a first direction and a second direction along a length of the handpiece; and a needle at least partially resident within the hub and the sleeve, wherein the needle is maintained at a fixed position relative to the handpiece, and wherein the hub includes a slidable portion.

2. The surgical handpiece of claim 1, wherein the needle is in communication with the handpiece.

3. The surgical handpiece of claim 1, wherein a plurality of ribs located on an inner portion of the sleeve are configured to engage communication with the outer portion of the hub.

4. The surgical handpiece of claim 1, wherein the sleeve comprises a plurality of openings comprising rounded edges.

5. The surgical handpiece of claim 1, wherein the hub further comprises a static portion, and wherein the slidable portion of the hub is configured to be slidably moved in the first direction and the second direction along the length of the handpiece.

6. The surgical handpiece of claim 1, wherein the hub is removably attached to the handpiece.

7. The surgical handpiece of claim 1, wherein the sleeve is removably attached to the hub.

8. The surgical handpiece of claim 1, wherein a distal end of the sleeve comprises a bullet-nose shape.

9. The surgical handpiece of claim 1, wherein the surgical handpiece is a phacoemulsification handpiece.

10. The surgical handpiece of claim 1, wherein the hub includes a retaining or locking member for retaining the hub and the sleeve in a particular position.

11. The surgical handpiece of claim 1, wherein the hub includes an alignment member for aligning the sleeve with the hub in a particular orientation.

12. The surgical handpiece of claim 1, further comprising an actuator configured to move the sleeve in the first direction and the second direction.

13. The surgical handpiece of claim 5, wherein the first static portion of the hub is threadedly coupled with the handpiece.

14. The surgical handpiece of claim 1, wherein the sleeve is configured to be frictionally coupled with the hub.

* * * * *